United States Patent
Makos

[11] Patent Number: 6,063,364
[45] Date of Patent: May 16, 2000

[54] TOOTH PASTE WITH INCLUDED APPLE CIDER VINEGAR FOR DAZZLING TEETH

[76] Inventor: Anne H. Makos, 2620 Martins La., Hellertown, Pa. 18055-3020

[21] Appl. No.: 09/050,408

[22] Filed: Mar. 30, 1998

[51] Int. Cl.[7] .............................. A61K 7/16; A61K 7/24
[52] U.S. Cl. ................................ 424/49; 424/55
[58] Field of Search .......................... 424/49–58

[56] References Cited

U.S. PATENT DOCUMENTS

| | | | |
|---|---|---|---|
| 3,812,272 | 5/1974 | Linville | 426/380 |
| 3,957,967 | 5/1976 | L'Orange | 424/49 |
| 4,082,841 | 4/1978 | Paper | 424/50 |
| 4,428,929 | 1/1984 | Wicheta et al. | 424/40 |
| 4,699,791 | 10/1987 | Tabord | 424/195.1 |
| 4,806,173 | 2/1989 | Toukan | 134/42 |
| 5,215,769 | 6/1993 | Fox et al. | 426/74 |
| 5,376,374 | 12/1994 | Zelaya | 424/195.1 |
| 5,662,888 | 9/1997 | Diamond | 424/49 |
| 5,772,986 | 6/1998 | Kruss | 424/53 |

OTHER PUBLICATIONS

Abstract of PILI WO/PCT 95/12380 Mouthwash Comprised of Vinegars Any Pird Apple Juices O, 40 L and 2 Teaspoons $NaHCO_3$ Hester Heath Whiten Teeth Make Gums Healthy, May 1995.

*Primary Examiner*—Shep K. Rose

[57] ABSTRACT

A toothpaste is improved and especially rendered a breath freshening agent by thoroughly mixing with a solution of three (3) parts of apple cider vinegar and one part of water, which final toothpaste mixture may then be applied to the teeth by brushing in the normal manner.

6 Claims, No Drawings

TOOTH PASTE WITH INCLUDED APPLE CIDER VINEGAR FOR DAZZLING TEETH

FIELD OF THE INVENTION

The present invention toothpaste and the like for brushing the teeth to clean the teeth and more particularly to a toothpastes with breath freshening ingredients and more particularly vinegar and preferably apple cider vinegar to combat disagreeable odors and malodorousness.

BACKGROUND OF THE INVENTION

Toothpastes for brushing or cleaning the teeth have been used for a great number of years. More recently not only ingredients to polish or clean the teeth, but to prevent decay and the like have been included in toothpastes and so-called breath fresheners, particularly mint tastes and odors have been used.

SUMMARY OF THE INVENTION

The invention includes the addition to and use of the ingredient vinegar and preferably apple cider vinegar to an ordinary toothpaste composition such vinegar being preferably diluted with one part water per every three parts of vinegar before mixing with the toothpaste to improve the results of using such toothpaste in the brushing of teeth and particularly to act as a combined breath freshener.

DESCRIPTION OF THE PREFERRED EMBODIMENTS

In the practice of the invention the Applicant mixes

ONE (1) teaspoon (OR ONE PART) OF WATER WITH THREE (3) TEASPOONS (OR THREE PARTS) OF WHITE APPLE CIDER VINEGAR. THIS MIXTURE IS THEN COMBINED AND THOROUGHLY MIXED WITH TOOTHPASTE.

THE RESULTANT PRODUCT, WHEN APPLIED TO A USER'S TEETH SIMPLY BY THE BRUSHING OF SUCH USER'S TEETH IN THE NORMAL MANNER, ELIMINATES ODORS (INCLUDING GARLIC), FRESHENS BREATH, WHITENS TEETH, REMOVES PLAQUE AND REDUCES CAVITIES.

What is claimed is:

1. A toothpaste containing an additive for enhancing the effectiveness of the toothpaste comprising:

(a) a toothpaste composition;

(b) a solution of one part water and three parts apple cider vinegar, (c) whereby the toothpaste is made more effective in cleaning the teeth and breath freshening.

2. A toothpaste with an additive in accordance with claim 1 wherein such one part water solution comprises one teaspoon of water and three parts apple cider vinegar comprises three teaspoons of apple cider vinegar thoroughly mixed together.

3. A toothpaste with enhanced cleaning and breath freshening properties comprising:

(a) a conventional toothpaste, and (b) a mixture of one part water and three parts fruit vinegar.

4. A toothpaste in accordance with claim 3 wherein such fruit vinegar comprises apple cider vinegar.

5. A method of making an improved toothpaste with enhanced cleaning and breath freshening properties comprising:

(a) formulating a mixture of one part of water and three parts cider vinegar, and (b) combining such mixture with a conventional formulation of toothpaste.

6. A method in accordance with claim 5 wherein the improved formulated toothpaste is thereafter used in the normal manner of toothpaste in brushing the teeth whereby odors are at least partially eliminated from the mouth, stains and plaque are removed from the teeth, the breath is freshened and cavity formation in the teeth are reduced.

* * * * *